US010548836B2

(12) United States Patent
Deroles et al.

(10) Patent No.: US 10,548,836 B2
(45) Date of Patent: *Feb. 4, 2020

(54) PIGMENT COMPOSITIONS COMPRISING ANTHOCYANIC VACUOLAR INCLUSIONS (71) Applicant: The New Zealand Institute for Plant and Food Research Limited, Mt. Albert (NZ)

(72) Inventors: Simon Christopher Deroles, Levin (NZ); Huaibi Zhang, Palmerston North (NZ); Kevin Davies, Manawatu (NZ)

(73) Assignee: The New Zealand Institute for Plant and Food Research Limited, Mt. Albert, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,589

(22) Filed: Apr. 24, 2018

(65) Prior Publication Data
US 2018/0235868 A1 Aug. 23, 2018

Related U.S. Application Data (63) Continuation of application No. 14/641,731, filed on Mar. 9, 2015, now Pat. No. 9,980,899, which is a continuation of application No. 12/934,941, filed as application No. PCT/NZ2009/000041 on Mar. 27, 2009, now abandoned.

(30) Foreign Application Priority Data

Mar. 28, 2008 (NZ) ........................................ 567036

(51) Int. Cl.
A61K 36/00 (2006.01)
A61K 8/97 (2017.01)
A61K 8/49 (2006.01)
C09B 61/00 (2006.01)
A23L 5/43 (2016.01)
A23K 20/179 (2016.01)
A61Q 90/00 (2009.01)
D06P 1/34 (2006.01)

(52) U.S. Cl.
CPC .............. A61K 8/97 (2013.01); A23K 20/179 (2016.05); A23L 5/43 (2016.08); A61K 8/498 (2013.01); A61K 36/00 (2013.01); A61Q 90/00 (2013.01); C09B 61/00 (2013.01); D06P 1/34 (2013.01); A61K 2800/10 (2013.01); A61K 2800/42 (2013.01); Y10T 442/20 (2015.04)

(58) Field of Classification Search
CPC .................................................... A61K 36/00
USPC ........................................................ 424/725
See application file for complete search history.

(56) References Cited

U.S. PATENT DOCUMENTS

| 2007/0166253 | A1 | 7/2007 | Kostick et al. |
| 2007/0166256 | A1 | 7/2007 | Shiroyama et al. |
| 2008/0050500 | A1 | 2/2008 | Muranishi et al. |
| 2008/0075797 | A1 | 3/2008 | LaPointe et al. |
| 2012/0115800 | A1 | 5/2012 | Zhang et al. |

FOREIGN PATENT DOCUMENTS

| JP | 2001-064531 | 3/2001 |
| JP | 2001-122730 | 5/2001 |
| JP | 2003-164754 | 6/2003 |
| WO | WO 2009/115023 | 9/2009 |
| WO | WO 2009/120097 | 10/2009 |
| WO | WO 2010/123383 | 10/2010 |

OTHER PUBLICATIONS

Andersen et al. (2006) "The Anthocyanins," In; Flavonoids: Chemistry, Biochemistry and Applications. Eds: Andersen, M.; Markham, K. CRC Press. pp. 471-551.
Asen et al. (1975) "Anthocyanin, Flavonol Copigments, and pH Responsible for larkspur flower colour," Phytochemistry. 14:2677-2682.
Bligh et al. (1959) "A Rapid Method of Total Lipid Extraction and Purification," Canadian Journal of Biochemistry and Physiology. 37(8):911-917.
Carrapiso et al. (2000) "Development in Lipid Analysis: Some New Extraction Techniques and in situ Transesterification," LIPIDS. 35(11):1167-1177.
Conn et al. (2003) "Anthocyanic Vacuolar inclusions (AVIs) selectively bind acylated anthocyanins in Vitis vinifera L. (grapevine) suspension culture," Biotechnology Letters. 25:835-839.
Cormier et al. (1993) "XXVII Vitis vinifera L. (grapevine): in vitro production of anthocyanins," Ch. 24. In; Biotechnology in Agriculture and Forestry, Medicinal and Aromatic Plants. Ed: Bajaj, Y.P.S. Springer Verlag. Berlin, Germany. pp. 373-386.
Deroles et al. (1998) "An antisense chalcone synthase cDNA leads to novel colour patterns in lisianthus (Eustoma grandiflorum) flowers", Molecular Breeding 4:59-66.
Douliez et al. (2006) "Novel Lipid System Forming Hollow Microtubes at High Yields and Concentration," Langmuir. 22:2942-2945.
Gebauer et al. (2006) "n-3 Fatty acid dietary recommendations and food sources to achieve essentiality and cardiovascular benefits," American Journal of Clinical Nutrition. 83:1526S-1535S.
Gonnet (2003) "Origin of the Color of Cv. Rhapsody in Blue Rose and Some Other So-called 'Blue' Roses," J. Agric. Food Chem. 51:4990-4994.
Harwood (2010) "Plant Fatty Acid Synthesis" The AOCS Lipid Library. http://lipidlibrary.aocs.org/plantbio/fa_biosynth/index.htm. [Last Accessed May 1, 2014].
Hemleben (1981) "Anthocyanin carrying structures in specific genotypes of Matthiola incana", R.Br. Z. Naturforsch. 36c:926-927.

(Continued)

Primary Examiner — Michael V Meller
(74) Attorney, Agent, or Firm — Leydig, Voit & Mayer, Ltd.

(57) ABSTRACT

The invention provides a pigment composition comprising anthocyanic vacuolar inclusions or "AVIs" from a plant, and an acceptable carrier. The invention also provides methods for colouring products with the pigment composition, and products comprising the pigment composition or AVIs.

8 Claims, 5 Drawing Sheets (56) References Cited

OTHER PUBLICATIONS

International Search Report with Written Opinion corresponding to International Patent Application No. PCT/NZ2009/000041, dated Jul. 28, 2009.

International Search Report with Written Opinion corresponding to International Patent Application No. PCT/NZ2010/000073, dated Jul. 21, 2010.

Jacob et al. (2008) "Physico-Chemical Characteristics of Nanovesicle-Carbohydrate Complexes in Grape Juice Concentrate," *Journal of Agricultural and Food Chemistry*. 56:1305-1315.

Kriat et al. (1993) "Analysis of plasma lipids by NMR spectroscopy: Applicastion to modifications incduced by malignant tumors," *J. Lipid Res*. 24:1009-1019.

Kubo et al. (1995) "Intravacuolar Spherical Bodies in *Polygonum cuspidatum*," *Plant Cell Physiol*. 36(8):1453-1458.

Lazaro et al. (1975) "Properties of Spinach Chloroplast Fructose-1,6-Diphosphatase," *Phytochemistry*. 14:2579-2583.

Liang et al. (2005) "Encapsulation of Lipopeptides Within Liposomes: Effect of Number of Lipid Chains, Chain Length and Method of Liposome Preparation," *International Journal of Pharmaceutics*. 301:247-254.

Markham et al. (2000) "Anthocyanic vacuolar inclusions—their nature and significance in flower colouration," *Phytochemistry*. 55:327-336.

Markham et al. (2004) "Black Flower Coloration in Wild *Lisianthius nigrescens*: Its Chemistry and Ecological Consequences," *Z. Naturforsch, Journal of Biosciences*. 59c:625-630.

Markham et al. (Aug. 2006) "Separation and Identification of Major Plant Sphingolipid Classes from Leaves," *J. Biol Chem*. 281(32):22684-22694.

Morgan (1998) "Callus Production from Protoplasts of *Cyclamen Persicum*," *Plant Cell, Tissue and Organ Culture*. 55:63-65.

Mulinacci et al. (2001) "Stabilisation of Natural Anthocyanins by Micellar Systems," *International Journal of Pharmaceutics*. 216:23-31.

Nozue et al. (1993) "Characterization of Intravacuolar Pigmented Structures in Anthocyanin-Containing Cells of Sweet Potato Suspension Cultures," *Plant Cell Physiol*. 34(6):803-808.

Nozue et al. (1995) "Detection and Characterization of a Vacuolar Protein (VP24) in Anthocyanin-Producing Cells of Sweet Potato in Suspension Culture," *Plant Cell Physiol*. 36:883-889.

Nozzolillo et al. (1988) "An investigation of the intracellular site of anthocyanoplasts using isolated protoplasts and vacuoles," *Plant Cell Rep*. 7:389-392.

Philpott et al. (2009) "Dietary Protection Against Free Radicals: A Case for Multiple Testing to Establish Structure-activity Relationships for Antioxidant Potential of Anthocyanic Plant Species," *International Journal of Molecular Sciences*. 10:1081-1103.

Small et al. (1982) "The ultrastructure in anthocyanoplasts in red-cabbage," *Planta*. 154:97-99.

Zhang et al. (2006) "New insight into the structures and formation of anthocyanic vacuolar inclusions in flower petals," *BMC Plant Biology*. 6:29.

Mizuno et al. (2006) "Effect of anthocyanin composition in grape skin on anthocyanic vacuolar inclusion development and skin coloration," Vitis. 45(4):172-177.

Wissgott et al. (1996) "Prospects for new natural food colorants," Trends in Food Science and Technology. 7:298-302.

Binding et al., (1977) "Regeneration of isolated protoplasts to plants in Solanum Dulcamara L." Z. Pflanzenphysiology 85:279-280.

PIGMENT COMPOSITIONS COMPRISING ANTHOCYANIC VACUOLAR INCLUSIONS

CROSS-REFERENCE TO RELATED APPLICATIONS

This patent application is a continuation application of U.S. Ser. No. 14/641,731 filed Mar. 9, 2015 which is a continuation application of U.S. Ser. No. 12/934,941 filed on Dec. 10, 2010. U.S. Ser. No. 12/934,941 is a US National Stage application based on PCT/NZ2009/000041, filed in English on Mar. 27, 2009, which claims the priority of New Zealand patent application No. 567036 filed on Mar. 28, 2008. Each of these applications is incorporated by reference herein in its entirety.

TECHNICAL FIELD

The invention relates to plant-derived pigment compositions, and applications thereof.

BACKGROUND ART

Attractive and stable colouration is an important factor in the marketability of foods and beverages. Synthetic colouring agents are often used in the food and beverage industry. However, the safety of synthetic colouring agents has been questioned. Consumer confidence in synthetic food colouring agents in general, has decreased. There thus exists a need for naturally occurring pigment compositions.

Anthocyanins are naturally occurring in many plants and can serve as pigments to impart a wide range of colours. Anthocyanin pigments are biodegradable and water soluble; in addition they are reported to possess antioxidant properties.

Despite such beneficial attributes, anthocyanin pigments have not been widely used as food additives for various reasons. Anthocyanins are difficult to purify which makes obtaining commercially useful quantities difficult. Anthocyanins are also degraded by unfavourable temperature, light and pH conditions.

The pH environment heavily influences the colour and stability of the anthocyanins, and it is this sensitivity in particular, that limits their use as a natural colourant. Under ideal pH conditions (acidic) anthocyanins are strongly coloured and relatively stable. However many processed foods such as dairy products and soft drinks are less acidic in nature. Isolated anthocyanins under these conditions can change colour and have much reduced longevity. It would be highly desirable to identify a source or form of anthocyanin pigments with improved performance as an additive for food and beverage products. Such pigments may also find use as natural dyes, for example for fabrics, and particularly in products that come into human contact, such as clothing and cosmetics.

It is an object of the invention to provide a source or form of anthocyanins useful in a pigment composition that overcomes at least one of the problems associated with the anthocyanin preparations of the prior art and/or at least to provide the public with a useful choice.

SUMMARY OF THE INVENTION

In a first aspect the invention provides a pigment composition comprising anthocyanic vacuolar inclusions or "AVIs" from a plant, and an acceptable carrier. Preferably the pigment composition comprises isolated AVIs.

Stability of Pigment Composition

In one embodiment the pigment composition, or AVI, is stable at acidic pH and 4° C. for at least about 24 hours, preferably at least about 72 hours, more preferably at least about 120 hours, more preferably at least about 240 hours, most preferably at least about 360 hours.

In a further embodiment the pigment composition, or AVI, is stable at acidic pH and 25° C. for at least about 24 hours, preferably at least about 72 hours, more preferably at least about 120 hours, more preferably at least about 240 hours most preferably at least about 360 hours.

In a further embodiment the pigment composition, or AVI, is stable at acidic pH and 37° C. for at least about 24 hours, preferably at least about 48 hours, more preferably at least about 72 hours, most preferably at least about 120 hours.

Preferably the pigment composition, or AVI, is stable over a pH range from about 2.5 to about 8.0, preferably from about 4.0 to about 7.0, most preferably from about 5.0 to about 6.0.

In a further embodiment the pigment composition, or AVI, is stable under high light intensity for at least about 48 hours, preferably at least about 72 hours, more preferably at least about 120 hours, most preferably at least about 168 hours.

Preferably high light intensity refers to light intensity of greater than about 10, more preferably greater than about 50, most preferably greater than about 90 umoles photons per m2 per sec.

Structure of AVIs in Pigment Composition

In a preferred embodiment the anthocyanic vacuolar inclusions (AVIs), in the composition, comprise:
a) at least one anthocyanin, and
b) at least one lipid.

Anthocyanin

In one embodiment the anthocyanin is a glycoside of an anthocyanidin.

Anthocyanidin Types

In one embodiment the anthocyanidin is selected from one of: cyanidin, peonidin, delphinidin, pelargonidin, petunidin, malvidin, 3-deoxyathocyanindins, and 6- and 8-hydroxyanthocyanidins, and hydroxylated, acylated, and methylated derivatives thereof.

In a preferred embodiment the anthocyanidin is selected from one of: cyanidin, peonidin, delphinidin, and pelargonidin, and hydroxylated, acylated, and methylated derivatives thereof.

In a preferred embodiment the acylation is aromatic acylation.

Glycoside Types

In one embodiment the anthocyanin is a glucoside of an anthocyanidin.

In a further embodiment the anthocyanin is a galactoside of an anthocyanidin.

In a further embodiment, the anthocyanin is a monoglycoside of the anthocyanidin.

In a further embodiment, the anthocyanin is a diglycoside of the anthocyanidin.

In a further embodiment the anthocyanin is an acylated glycoside of the anthocyanidin.

In a further embodiment, the anthocyanin is an acylated monoglycoside of the anthocyanidin.

In a further embodiment, the anthocyanin is an acylated diglycoside of the anthocyanidin.

In a further embodiment the anthocyanin has O-glycosylation at one or more of the 3-, 5-, 7-, 3'- or 5' positions.

In a preferred embodiment the anthocyanin has O-glycosylation and acylation at one or more of the 3-, 5-, 7-, 3'- or 5' positions.

In a more preferred embodiment the anthocyanin is a 3- or 5-O-glycoside.

In a more preferred embodiment the anthocyanin is a 3,5-di-O-glycoside.

In a more preferred embodiment the anthocyanin is a 3,5-di-O-glycoside with acylation.

In one embodiment the pigment composition comprises at least one anthocyanin selected from those listed in Table 2.

In a further embodiment the pigment composition comprises at least one anthocyanin selected from those from lisianthus listed in Table 2.

In a preferred embodiment the acylation is aromatic acylation.

Lipid

In one embodiment the lipid is a biological membrane or biomembrane.

In a further embodiment the lipid is part of a biological membrane or biomembrane.

In a preferred embodiment the lipid is a fatty acid.

Structure Independent of Stability

Compositions comprising AVIs with the described structure but without the described stability, products comprising the compositions or AVIs and methods of use of the AVIs and compositions, are also included within the scope of the invention.

The AVIs May Comprise Mixtures of Different Types of Anthocyanin

A mixture of different anthocyanins, including at least one type as discussed above (the first anthocyanin), and one or more additional anthocyanins, may also be in the AVIs, compositions and products of the invention.

In one embodiment the additional anthocyanin/s is of a type discussed above, but different from the first anthocyanin.

Products

In a further aspect the invention provides a food product comprising a pigment composition of the invention.

In a further aspect the invention provides a cosmetic product comprising a pigment composition of the invention.

In a further aspect the invention provides fabric coloured with a pigment composition of the invention.

In a further aspect the invention provides a topical cream comprising a pigment composition of the invention.

In a further aspect the invention provides a food product comprising anthocyanic vacuolar inclusions or "AVIs" from a plant. Preferably the food product comprises isolated AVIs.

In a further aspect the invention provides a cosmetic product comprising anthocyanic vacuolar inclusions or "AVIs" from a plant. Preferably the cosmetic product comprises isolated AVIs.

In a further aspect the invention provides fabric coloured with anthocyanic vacuolar inclusions or "AVIs" from a plant. Preferably the fabric is coloured with isolated AVIs. In a further aspect the invention provides a topical cream comprising anthocyanic vacuolar inclusions or "AVIs" from a plant. Preferably the topical cream comprises isolated AVIs.

Preferably the AVIs used in the food product, cosmetic product, topical cream or in colouration of fabric are stable at acidic pH for at least about 24 hours, preferably at least about 48 hours, more preferably at least about 72 hours, more preferably at least about 120 hours, most preferably at least about 168 hours.

Preferably the AVIs used in the food product, cosmetic product, topical cream or in colouration of fabric are stable at acidic pH and 4° C. for at least about 24 hours, preferably at least about 72 hours, more preferably at least about 120 hours, more preferably at least about 240 hours, most preferably at least about 360 hours.

Preferably the AVIs used in the food product, cosmetic product, topical cream or in colouration of fabric are stable at acidic pH and 25° C. for at least about 24 hours, preferably at least about 72 hours, more preferably at least about 120 hours, more preferably at least about 240 hours, most preferably at least about 360 hours.

Preferably the AVIs used in the food product, cosmetic product or in colouration of fabric are stable at acidic pH and 37° C. for at least about 24 hours, preferably at least about 48 hours, more preferably at least about 72 hours, most preferably at least about 120 hours Preferably the AVIs used in the food product, cosmetic product, topical cream or in colouration of fabric are stable over a pH range from about 2.5 to about 8.0, preferably from about 4.0 to about 7.0, most preferably from about 5.0 to about 6.0.

In a further embodiment the AVIs used in the food product, cosmetic product or in colouration of fabric are stable under high light intensity for at least about 48 hours, preferably at least about 72 hours, more preferably at least about 120 hours, most preferably at least about 168 hours.

Preferably high light intensity refers to light intensity of greater than about 10, more preferably greater than about 50, most preferably greater than about 90 umoles photons per m2 per sec.

The AVIs in the pigment composition, food product, cosmetic product, topical cream or used in colouration of fabric may be derived from any plant that contains AVIs. In a preferred embodiment the AVIs are isolated from a lisianthus species. Preferably the AVIs are isolated from *Eustoma grandiflorum*.

Methods

In a further aspect the invention provides a method of colouring a product, the method comprising adding a pigment composition of the invention to the product.

In one embodiment the product is selected from a food product, cosmetic product, topical cream, or a fabric.

In a further aspect the invention provides a method of colouring a product, the method comprising adding an AVI as herein defined to the product.

In one embodiment the product is selected from a food product, cosmetic product, topical cream, or a fabric.

DETAILED DESCRIPTION

1. General Definitions

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

2.0 AVIs

Anthocyanin pigments most commonly accumulate in the plant cell vacuole and are responsible for many of the colours in petals and fruits within the red to blue range. In most plant species the anthocyanins remain in solution and are evenly distributed within the vacuole. However in some species the anthocyanins are aggregated into small bodies within the vacuole, which enhances the cells ability to accumulate large amounts of anthocyanin. These anthocyanin-containing bodies have been described under several different names in a range of plant tissues as shown in Table 1. Such anthocyanin-containing bodies are referred to here as "anthocyanic vacuolar inclusions" or "AVIs".

TABLE 1

| Plant Species and Tissue | Description | Reference |
|---|---|---|
| Rose petals | AVIs | Gonnet, 2003 |
| Polygonium cuspidatum seedlings | Intravacuolar spherical bodies | Kubo et al., 1995 |
| Matthiola incana petals | Crystals | Hemleben, 1981 |
| Consolida ambigua petals | Blue crystals | Asen et al., 1975 |
| Mung bean hypocotyl | Red crystals | Nozzolillo and Ishikura, 1988 |
| Red cabbage leaves | Anthocyanoplasts | Small and Pecket, 1982 |
| Ipomea batatas tubers | Cyanoplasts | Nozue et al., 1995 |
| Grape cell cultures | Anthocyanoplasts | Cormier and Do, 1993 |

Anthocyanic vacuolar inclusions have also been described by Markham et al., (2000) and Zhang et al., (2006). The same papers describe methods for the isolation of AVI's from Purple lisianthus (*Eustoma grandiflorum*) and the Blue-grey carnation (*Dianthus caryophyllus*) and are incorporated herein by reference.

AVIs are globular or irregular in shape. AVIs display different colours according to their anthocyanin composition.

3.0 AVIs in the Pigment Composition of the Invention

The present invention results from the surprising discovery that the colour intensity of AVI-bound anthocyanins is stable under environmental conditions normally associated with a loss of the colour intensity of free, or un-bound, anthocyanins.

The applicants have elucidated the structure/composition of AVIs. The applicants have shown that anthocyanins and lipids are the two main classes of compounds found in the AVIs.

Preferably the "anthocyanic vacuolar inclusion" or "AVI" as used herein means a structure found in the vacuole in a plant, comprising an anthocyanin and a lipid.

The lipid may be part of a biological membrane or biomembrane.

The biological membrane or biomembrane may also include other components such as proteins and sugar groups.

3.1 Stability of the AVIs in the Pigment Composition of the Invention

Preferably, the anthocyanin is more stable when part of the AVI, than when not part of the AVI, such as when in solution.

Preferably, the lipid is more stable (less susceptible to oxidation) when part of the AVI, than when not part of the AVI, such as when in solution.

Typically both the anthocyanin and the lipid are more stable when forming part of an AVI than they are when either the anthocyanin or lipid are separate, such as in solution.

The term "stable" in relation to AVIs or AVI containing pigment compositions refers to a reduced rate of loss of anthocyanic colour in environments normally associated with a loss of anthocyanic colour. Preferably stable refers to retention of at least 50% (more preferably at least 60%, more preferably at least 70%, more preferably at least 80%, more preferably at least 90%) of the anthocyanin's colour (as defined by optical density at 530 nm) under the specified conditions.

The term "stable" in relation to AVI containing pigment composition refers to the stability of the AVIs in the pigment composition.

3.2 Structure of the AVIs in the Pigment Composition of the Invention

AVIs are typically composed of single or multiple forms of anthocyanin molecules that are bound to by a lipid (such as a fatty acids or biomembranes), where such an interaction results in the increased stability of both the anthocyanins, and preferably also the lipid.

The term "anthocyanic vacuolar inclusion" or "AVI" preferably means a structure comprising of an anthocyanin molecule(s) that is (are) bound together by a lipid, where such an interaction results in the increased stability of the anthocyanin molecule (when compared to the anthocyanin molecule on its own in solution) under varying conditions such as (but not limited to) pH, temperature, light intensity. The AVI may also include additional substances such as phenlypropanoids, proteins, carbohydrates and inorganic compounds.

The term "anthocyanins" means glycosides of any of anthocyanidins, including but not limited to, pelargonindin, cyanidin, peonidin, delphinidin, petunidin, malvidin, 3-deoxyathocyanindins, and 6- and 8-hydroxyanthocyanidins, and hydroxylated, acylated, and methylated derivatives thereof. Preferably the glycosides are glucosides or galactosides. Preferably the acylation is aromatic acylation.

Preferably, the anthocyanin has O-glycosylation at one or more of the 3-, 5-, 7-, 3'- or 5' positions, more preferably the anthocyanin has O-glycosylation and acylation at one or more of the 3-, 5-, 7-, 3'- or 5' positions, more preferably the anthocyanin is a 3- or 5-O-glycoside, more preferably the anthocyanin is a 3,5-di-O-glucoside, and most preferably the anthocyanin is a 3,5-di-O-glycoside with acylation. Preferably the acylation is aromatic acylation.

4.0 Isolation of AVIs

AVIs may be isolated from plants by various methods. For example AVIs may be isolated from flower petals using variations of the method of Markham et al., (2000), and methods described in the examples section of this specification.

An example of such an isolation procedure is provided as follows:

Healthy petals are excised from fully open flowers and subsequently washed thoroughly with cold tap water containing several drops of Tween 20, followed by rinsing with distilled water.

The washed petals are then chopped up using an onion chopper on a plastic board until the petals became a slurry. Small amounts of phosphate buffer (0.1 M, pH 7.0) containing 10 mM EDTA were added during the chopping. The petal slurry is then added to a macerating solution containing 1% cellulase Onozuka R-10 (Yakult Honsha Co., Higashi-Shinbashi, Minatoku, Tokyo) and 0.05% Pectolyase Y23. The mix is incubated overnight at room temperature to release protoplasts containing AVIs.

The incubated mix is subsequently filtered through 50 μm cheesecloth and washed by vortexing in 0.1 M phosphate buffer plus 17.53 g/L sodium chloride (wash solution). The AVI-containing protoplasts are then collected by centrifugation at 100 g for 5 min. The wash step is repeated two more times and the final pellet is suspended in a minimal volume of wash solution.

The suspended pellet is then transferred into a new tube containing 80% Percoll (AMRAD-Pharmacia Biotech, Auckland, New Zealand). The AVI pellet is harvested from the bottom of the centrifuge tube after centrifugation at 10,000 g for 10 min. The pellet is washed twice in wash solution and then stored −80° C. until use.

The term "isolated" with reference to AVIs means purified relative their concentration in intact plant material, or in macerated non-fractionated plant material. Preferably the isolated AVIs are at least about 10% pure, more preferably at least about 20% pure, more preferably at least about 30% pure, more preferably at least about 40% pure, more preferably at least about 50% pure, more preferably at least about 60% pure, more preferably at least about 70% pure, more preferably at least about 80% pure, more preferably at least about 90% pure, more preferably at least about 95% pure, most preferably at least about 99% pure.

5.0 Components of Pigment Compositions

The term "acceptable carrier" with reference to the pigment composition of the invention means a component, additional to the AVI itself, which is acceptable for the composition's application. Acceptable carriers include but are not limited to solvents, buffers and preservatives.

Acceptable carriers for use in the pigment composition for food product applications are known to those skilled in the art and include but are not limited to:

Water-Soluble Carriers:

Gums, Carrageenan, Gum Arabic, Alginates, Ammonin alginate, Potassium alginate, Sodium alginate, Starches, Maltodextrins, Sucrose, Dextrose, Fructose, Syrups, Alcohols, Glycerol, Sodium carbonate, Sodium hydrogen carbonate, Ethyl cellulose, Microcrystalline cellulose, Cellulose, Powdered Benzyl alcohol, Ethyl Alcohol (ethanol), Ethyl Acetate, Lactose starch, Citric Acid, Diethyl Tartrate, Lactic acid ethyl ester, Magnesium Carbonate, Magnesium Hydrogen Carbonate, Polydextrose, Polyethylene Glycol, Polyoxyethylene (20) Sorbitan Monolaurate, Polyoxyethylene (20) Sorbitan Monooleate, Polyoxyethylene (20) Sorbitan Monopalmitate, Polyoxyethylene (20) Sorbitan Monostearate, Polyoxyethylene (20) Sorbitan Tristearate, Polyvinylpyrrolidone, Propan-2-Ol, Propylene glycol, and Silicon Dioxide.

Oil Soluble Carriers:

Edible fats and oils, Medium chain triglycerides, Bees' wax, Paraffin, Shellac, Rosin, 6-Palmitoyl-L-ascorbic acid, Amyl Acetate, Butane-1,3-Diol, Diethylene Glycol Monoethyl Ether, Isopropyl Myristate, Triacetin, and Ethyl Citrate.

Acceptable carriers for use in the pigment composition for cosmetic product applications are known to those skilled in the art.

Acceptable carriers for use in the pigment composition for textile colouring applications are known to those skilled in the art.

6. Preparation of the Pigment Compositions of the Invention

Pigment composition comprising AVIs may be prepared by methods known to those skilled in the art.

For example, the pigment composition can be sold as an additive for food or other products and can be prepared in dry, e.g., powdered, form or as a water or alcohol-based concentrate or syrup depending on the end use and the proposed method of addition.

The pigment composition of the invention may be added to food products by methods known in the art.

The pigment composition may be combined with one or more spray drying aids such as gum arabic and maltodextrins or the solution may be encapsulated by standard coascervation techniques in edible materials using gelatin.

The pigment composition may be added in conjunction with other materials such as flavouring adjuvants.

The pigment composition can be incorporated as a solid or an aqueous solution or syrup at various stages during the manufacture or processing of the food product.

The AVIs can be incorporated to food and beverage products in many ways, such as but not limited to:
   direct mixing via batch (tanks/blenders), using rotational impellers in aqueous materials.
   continuous or inline mixers in aqueous materials.
   dry blending into convenience foods for reconstitution by the consumer.
   coating the exterior surfaces of products through spraying, enrobing, and pan coating.

The AVIs and the carriers may need to be pre-dissolved in water to ensure maximum dispersibility and even mixing during food and beverage product manufacture. Small amounts of highly concentrated AVIs may be dispersed in icings (sugar/fat blends).

Due to their stable nature, the AVIs can be added to the early stages of production, ensuring they are distributed evenly, while maintaining optimal visual appeal.

AVIs can be used in combination with other food colouring materials to obtain the desired colour in the finished product.

7.0 Products

The term "food product" as used herein includes solid foods, liquid beverages and other edible materials regardless of their specific form. The term food product includes products that are chewed without being swallowed. Preferred food products include but are not limited to dairy products, such as yoghurts.

The present invention is not limited to use of the pigment compositions or AVIs in food products. Use of AVIs or AVI-containing compositions to colour other products such as cosmetics, topical creams, fabrics, and particularly products such as clothing and cosmetics that come into human contact, are included within the scope of the invention.

BRIEF DESCRIPTION OF THE DRAWINGS

The present invention will be better understood with reference to the accompanying drawings in which.

The invention will now be illustrated with reference to the following non-limiting examples.

EXAMPLES

Example 1 Isolation of AVIs from Plants

Plant Material

The lisianthus lines used in this study were lines #54 and Wakamurasaki (see Deroles et al. 1998 for further details). Fully open flowers were harvested and washed with distilled water to remove potential contaminants such as pollen grains. Various petal regions were excised with a razor blade for further study.

Lisianthus AVIs are found as one or more large irregular shapes in the vacuoles of adaxial epidermal cells in the throat of the flower. The lisianthus AVIs could be removed from cell vacuoles using narrow glass micropipettes. They remained intact, and adhered firmly to glass indicating that they are structural rather than localized concentrations of dissolved anthocyanins. In addition, electron microscopy images show that the AVI body is not membrane bound.

Protoplast Generation and Isolation

Protoplasts were generated from macerated inner petal material as described by Morgan (1998). Material from 10 flowers was added to a protoplasting solution containing 1% cellulose Onozuka R-10 (Yakult Honsha Co., Higashi-Shinbashi, Minatoku, Tokyo) and 0.05% Pectolyase Y23. The mix was incubated overnight at room temperature and then filtered through a 50 μm stainless steel mesh, washed in $\frac{1}{10}$ strength VKM macro salts (Binding and Nehls. 1977) plus 17.53 g/l NaCl (wash solution), and the protoplasts collected by centrifugation (100×g, 5 min). The pelleted protoplasts were washed twice with wash solution.

AVI Isolation

To enrich for protoplasts containing the AVIs, isolated protoplasts were subjected to centrifugation through a 4 step discontinuous Percoll (AMRAD-Pharmacia Biotech, Auckland, NZ) gradient (20%, 30%, 50%, 80% v/v, Percoll/wash solution). The gradient was formed by careful sequential addition of equal volumes of each gradient solution in descending order. Isolated protoplasts in wash solution were added to the top of the gradient and the gradient developed by centrifugation (300×g, 5 min in a swing-out bucket rotor). Intensely pigmented protoplasts containing AVIs were collected from the 50%/80% boundary and washed twice with wash solution. The AVI-containing protoplasts were lysed using sonication and the product was carefully layered onto a second Percoll gradient that was developed as described above. Isolated AVIs pelleted at the bottom of the centrifuge tube and were washed twice with wash solution.

For use in control experiments anthocyanins were leeched from AVIs under acidic conditions (90% MeOH/5% Acetic Acid).

Example 2 Stability of AVI-Bound Anthocyanins in a Range of pH Environments

AVIs isolated from lisianthus were resuspended in a McIlvaines buffer (Citric Acid/Sodium Phosphate) array from pH 3.0 to 8.0. The samples were left at room temperature and lighting conditions (fluorescent/natural light) for up to 7 days to determine the stability and colourfastness of the AVI-bound anthocyanins. A spectrum of each sample (350-750 nm) was taken at daily intervals to determine the hue and intensity of the AVI-bound anthocyanins over time. In the control experiment, anthocyanins were extracted from the AVIs and subjected to the same pH conditions.

Figure 1:
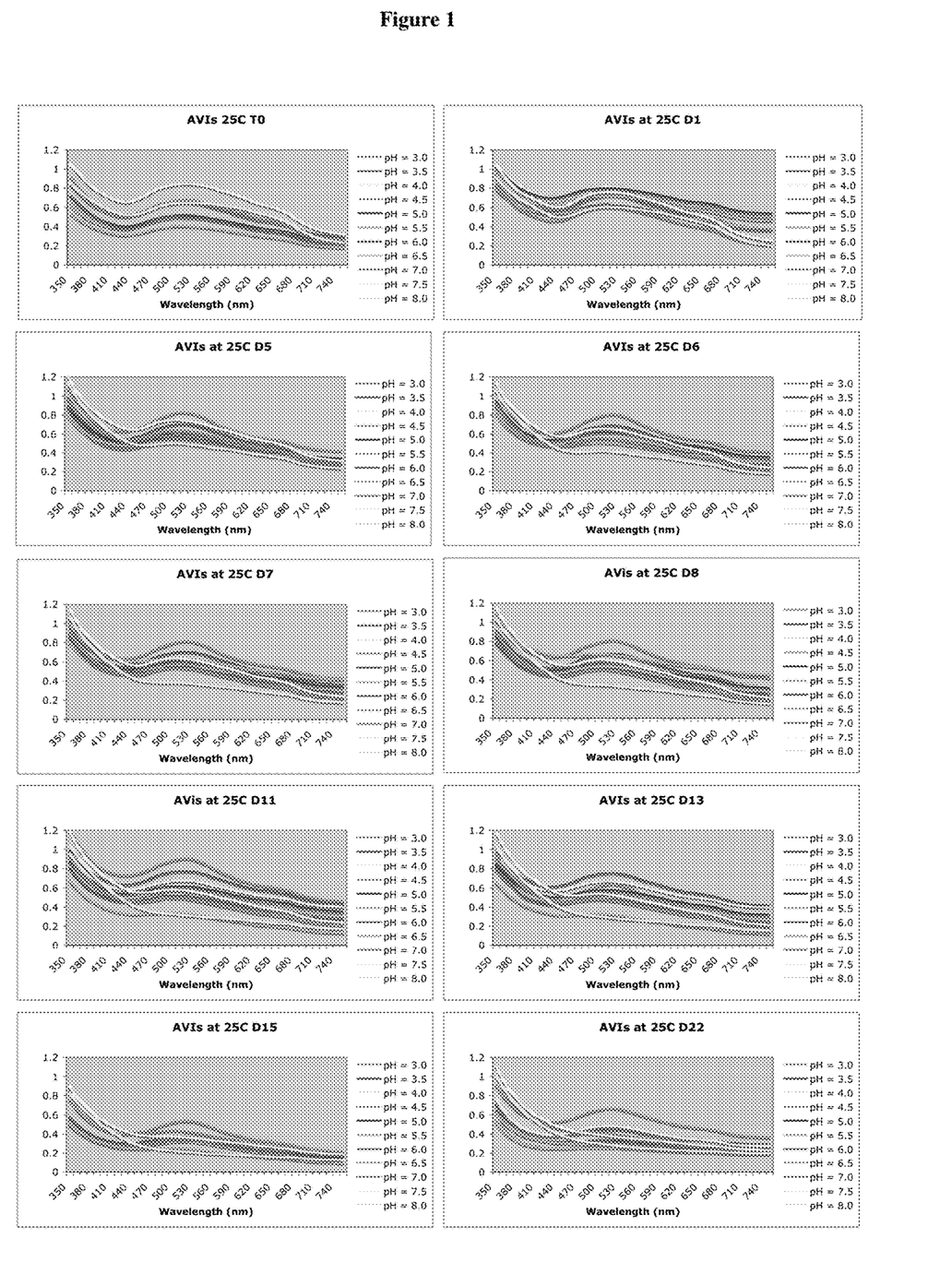
FIG. 1 shows the absorbance spectra of AVI-bound anthocyanins resuspended in water and pH buffers ranging from 3.0-8.0 over a period of 22 days. The samples were incubated at room temperature under room lighting conditions (natural/fluorescent light). T1=1 hour, D1=1 Day, D2=2 days –D7=7 days

As shown in FIG. 1 the anthocyanins in this experiment have maintained their colour over a wide pH range and for a significant period of time. All the other treatments do not change significantly until 7 days where the samples at more alkaline pH levels (pH 6-8) begin to fade.

Figure 2:
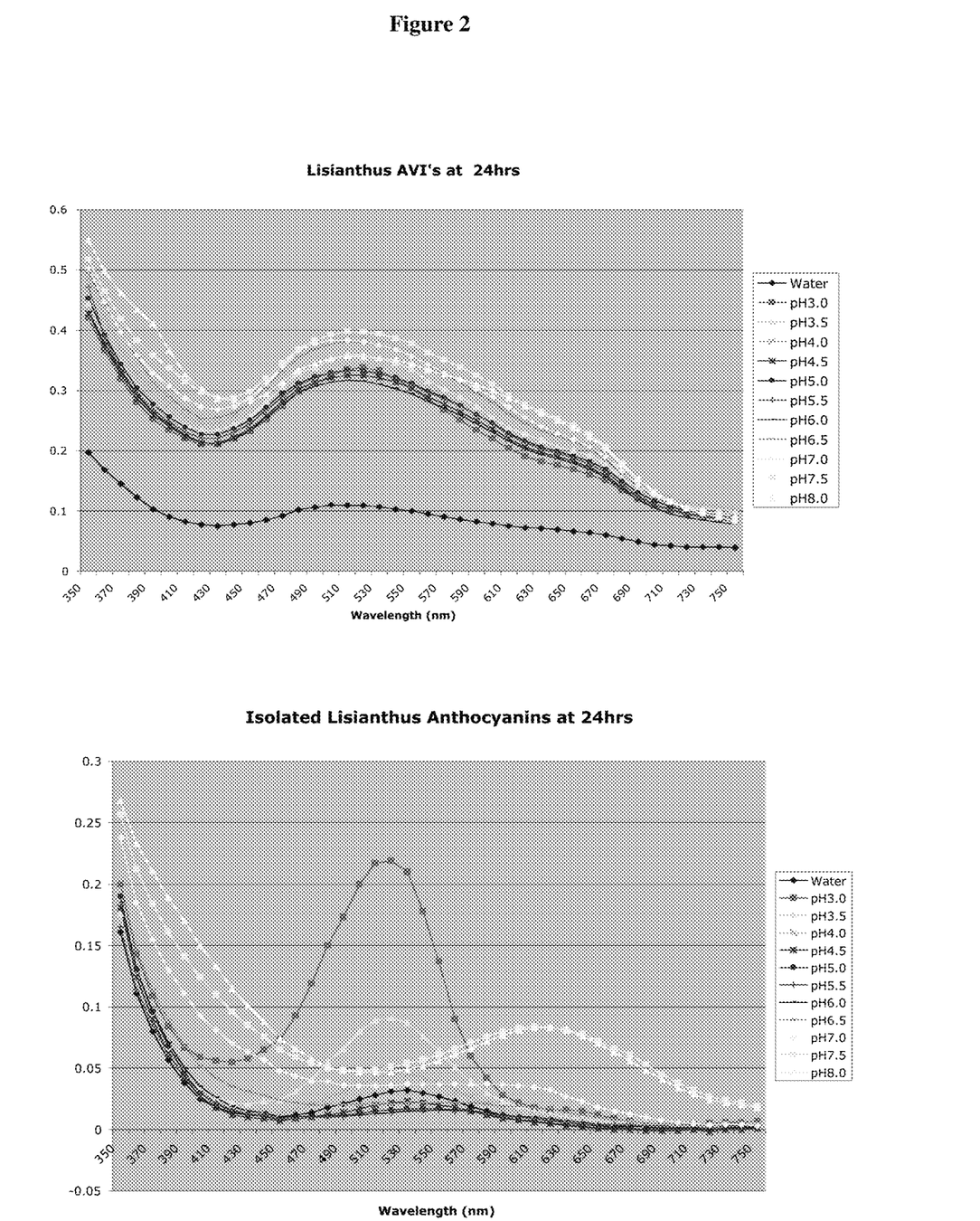
FIG. 2 shows the absorbance spectra of anthocyanins, bound and unbound to AVIs that were resuspended in water and pH buffers ranging from 3.0-8.0 over a period of 24 hours. The samples were incubated at room temperature under room lighting conditions (natural/fluorescent light).

Anthocyanins were then extracted from the lisianthus AVIs and resuspended in the pH buffer array used previously. A sample of intact AVIs was also treated at the same time. Again, the absorbance spectrum of the AVI-bound anthocyanins does not change significantly over the pH range, or over a 24-hour period as shown in FIG. 2. However the same anthocyanins, when released form the AVI structures behave in a more predictable manner in that they have significantly different absorbance spectra according to the pH of the solution and their spectra also changed over time. This demonstrates clearly that the lisianthus AVI structure effectively protects bound anthocyanins from the effects of differing pH environments.

Example 3 Stability of AVI-Bound Anthocyanins in Commercial Natural Yoghurt

AVIs from lisianthus were mixed with a commercial natural yoghurt sample (pH 4.18) obtained from a supermarket in order to determine their ability to maintain colour in a processed food environment. The samples were left at room temperature under room lighting conditions for 24 to 48 hours.

Figure 3:
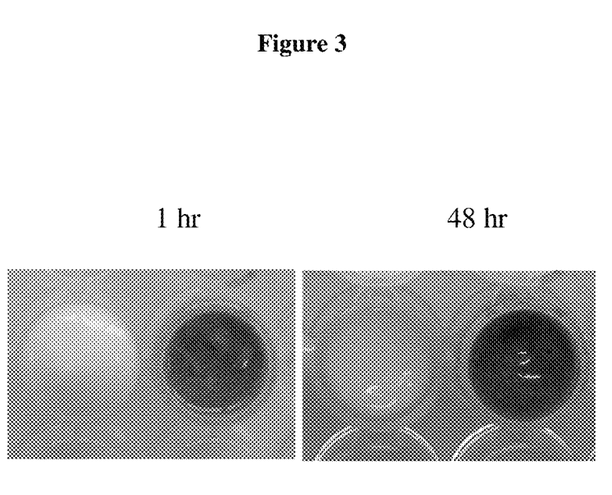
FIG. 3 shows lisianthus AVIs resuspended in natural yoghurt and left at room temperature under room lighting conditions (natural/fluorescent light) for 24 and 48 hours.

As shown in FIG. 3, the lisianthus AVIs were able to maintain their colour over a 48-hour period.

Example 4: Elucidation of AVI Structure/Composition

Isolation of AVIs from Carnation and Lisianthus

Plant Material

Carnation (a mauve coloured cultivar of *Dianthus caryophyllus*) or Lisianthus (#54 cultivar of *Eustoma grandiflorum*) were grown in the glasshouse under the conditions of natural lighting and day length. Fully expanded flower petals were collected and washed to remove unwanted contaminants.

Carnation AVIs are more round-shaped throughout the petal than the more irregular shaped AVIs of lisianthus. Carnation AVIs are found throughout the petals. The structure of AVIs was previously unknown. The applicants hypothesised that although AVIs do not have surface membranes to contain them, they may have infrastructural membranes or lipids. The applicants have now shown that anthocyanins and lipids are the two major components of AVIs as described below.

AVIs were isolated as follows:

Protoplast Preparation
1) The washed flower petals were mechanically macerated using an onion chopper or razor-blade to form a slurry. Subsequently, the slurry was incubated in an enzyme solution comprising 1% cellulase Onozuka R-10 (Yakult Honsha Co., Higashi-Shinbashi, Minatoku, Tokyo) and 0.05% pectolase Y23 (Morgan, 1998). The enzymatic maceration was carried out overnight at room temperature.
2) AVI-containing protoplasts were enriched by filtering the enzymatically macerated slurry through cheese cloth or metal screens with pore sizes that allow AVI containing protoplasts to pass. The AVI-containing protoplasts were then washed with buffers in which any released AVIs are stable, for example, 0.1 phosphate buffer containing 17.53 g/L sodium chloride. The AVI-containing protoplasts were then concentrated into a loose pellet by centrifuging.
3) The AVI-containing pellet was then transferred into 80% percoll (AMRAD-Pharmacia Biotech, Auckland, New Zealand). AVIs were released from the protoplasts by vortexing or gentle ultrasonic suspension treatment.

Elucidation of the Structure of AVIs

Anthocyanin Analysis

For anthocyanin analysis, the AVIs, prepared according to the procedures described above, were extracted with 80% methanol with 5% acetic acid. The extract was then subjected to LC-MS analysis. Table 2 below lists the anthocyanins found in the carnation and lisianthus AVIs.

TABLE 2

| | [M + H]+ |
|---|---|
| Lisianthus AVIs (purple) | |
| Cyanidin-3-O-glucoside | 449 |
| Delphinidin-3-O-glucoside | 465 |
| Cyanidin-3-O-galactoside-5-O-(6-O-p-coumaroylglucoside) | 757 |
| Cyanidin-3-O-galactoside-5-O-(6-O-ferulylglucoside) | 787 |
| Delphinidin-3-O-galactoside-5-O-(6-O-p-coumaroylglucoside) | 773 |
| Delphinidin-3-O-galactoside-5-O-(6-O-ferulylglucoside) | 803 |
| Cyanidin-O-coumaroylglucoside | 595 |
| Delphinidin-O-coumaroylglucoside | 611 |
| Delphinindin-3-O-acetylglucoside-5-O-glucoside(or galactoside) | 669 |
| Peonidin-3-O-rhamnogalactoside-5-O-(6-O-p-coumaroylglucoside) | 813 |
| Delphinidin-3-O-galactoside-5-O-(6-O-p-coumaroylglucoside) + m/z 123 | 896 |
| Cyanidin-3-O-galactoside-5-O-(6-O-p-coumaroylglucoside) + m/z 155 | 912 |
| Delphinidin-3-O-rhamnogalactoside-5-O-(6-O-p-coumaroylglucoside) | 919 |
| Cyanidin-3-di-O-galactoside-5-O-(6-O-p-coumaroylglucoside) | 919 |
| Delphinidin-3-O-galactoside-5-O-(6-O-ferulylglucoside) + m/z 123 | 926 |
| Delphinidin-3-di-O-galactoside-5-O-(6-O-p-coumaroylglucoside) | 935 |
| Cyanidin-3-O-galactoside-5-O-(6-O-ferulylglucoside) + m/z 155 | 942 |
| Delphinidin-3-O-rhamnogalactoside-5-O-(6-O-ferulylglucoside) | 949 |
| Cyanidin-3-di-O-galactoside-5-O-(6-O-ferulylglucoside) | 949 |
| Delphinidin-3-di-O-galactoside-5-O-(6-O-ferulylglucoside) | 965 |
| Pelargonidin-3-O-galactoside-5-O-(6-O-p-coumaroylglucoside) | 741 |
| Pelargonidin-3-O-galactoside-5-O-(6-O-ferulylglucoside) | 771 |

TABLE 2-continued

| | [M + H]+ |
|---|---|
| Carnation AVIs | |
| Pelargonidin | 271 |
| Pelargonidin-3-O-glucoside | 433 |
| Pelargonidin-3,5-di-O-glucoside | 595 |

Figure 4:
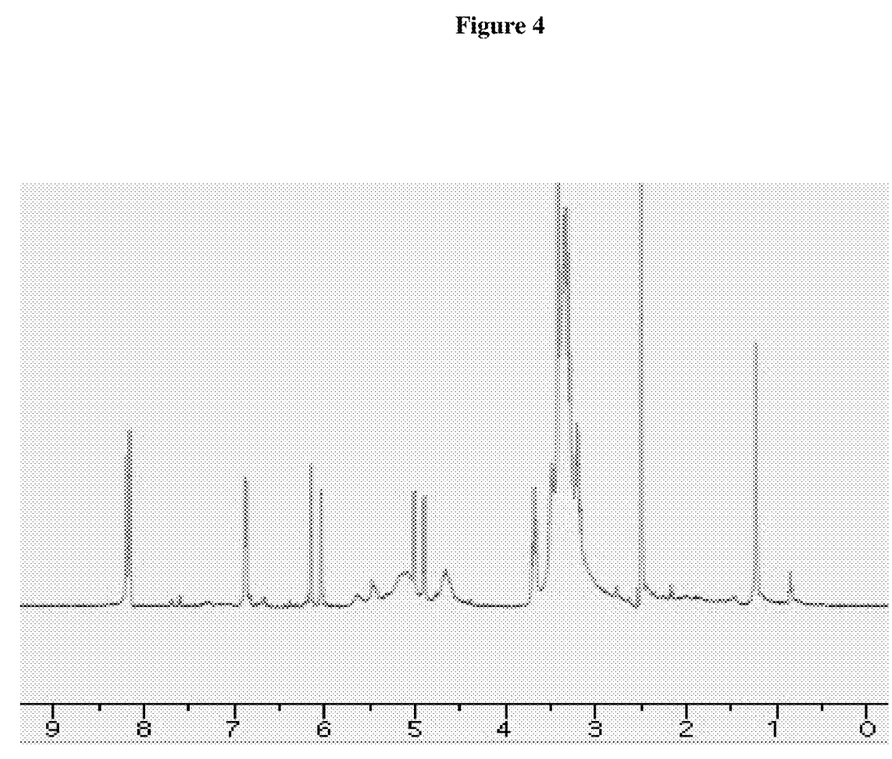
FIG. 4. NMR spectrum of carnation purified AVIs in DMSO solvent. The two peaks around chemical shift 1.0 ppm are from lipids present in AVIs. The major peaks between chemical shifts 2.0-9.0 ppm are from pelargonidin-3,5-di-O-glucoside present in the AVIs.

Freeze dried carnation and lisianthus AVIs were separately dissolved in DMSO-D6 and subjected to NMR analysis. FIG. 4 shows a NMR spectrum clearly reflecting the presence of pelargonidin 3, 5-di-O-glucoside and another major component.

Lipid Analysis

To confirm the presence of lipids in the AVIs, lipids were isolated from both carnation and lisianthus AVIs using an organic solvent: chloroform:methanol:TFA (50:50:0.5 v:v:v). Freeze-dried AVIs were dissolved with the organic solvent. Subsequently, the organic solvent containing dissolved AVIs was partitioned against acidified water (water with 0.5% TFA). The process was repeated several times until no anthocyanic colour was obvious in the organic phase. The organic phase containing lipids was collected, and was subsequently dried under nitrogen to prepare lipids. The dried lipids were then dissolved in a chloroform (d4) and methanol to carry out NMR measurement.

Figure 5:
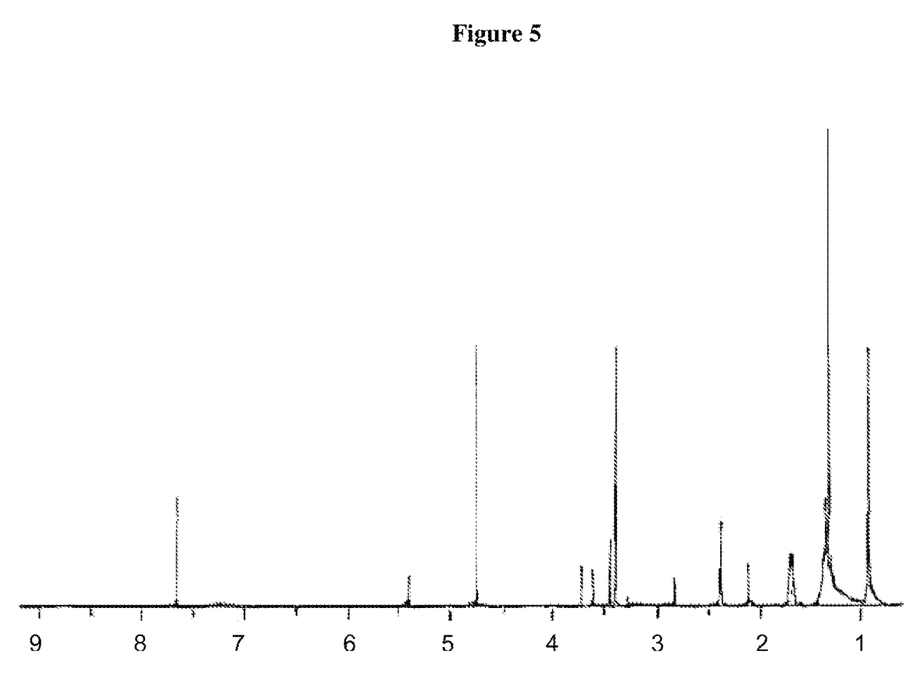
FIG. 5. NMR spectrum of lipids isolated from carnation AVIs. The lipids were dissolved in a mixture of 50% methanol and 50% chloroform. The peaks at the chemical shifts of 3.4, 4.7 and 7.6 ppm are due to the solvents and all the rest reflect from the lipids.

FIG. 5 shows the NMR spectrum of the extracted lipids from AVIs. Proton Nuclear Magnetic Resonance ($^1$H NMR) Spectroscopy of total lipids extracted from carnation AVIs displayed a typical upfield region of lipids extracted from a biological membrane sample (Kriat M, et al. 1993). The most prominent $^1$H NMR peak at 1.3 ppm is —(CH$_2$)n in fatty acyl chain. The peak at 0.9 ppm is characteristic of —CH$_3$ in fatty acyl chain. The peak at 1.6 ppm represents the bold italic H in the —CO—CH$_2$—CH$_2$; at 2.1 ppm CH$_2$CH═CH—; at 2.3 ppm —CH$_2$—COO—; at 2.8 ppm═CHCH$_2$CH— (polyunsaturated fatty acyl signal); at 3.6 ppm —CH$_2$—N+; at 5.4 ppm —CH═CH— in fatty acyl chain.

The above examples illustrate practice of the invention. It will be well understood by those skilled in the art that numerous variations and modifications may be made without departing from the spirit and scope of the invention.

REFERENCES

Asen, S., Stewart, R. N., Norris, K. H., 1975. Anthocyanin, flavonol co pigments, and pH responsible for larkspur flower colour. Phytochemistry 14, 2677-2682.

Cormier, F., Do, C. B., 1993. XXVII *Vitis vinifera* L. (grapevine): in vitro production of anthocyanins. In: Bajaj, Y. P. S. (Ed), Biotechnology in Agriculture and Forestry, Vol. 24, Medicinal and Aromatic Plants, V. Springer Verlag, Berlin, pp. 373-386.

Gonnet J-F., 2003. Origin of the Color of Cv. Rhapsody in Blue Rose and Some Other So-called "Blue" Roses. J. Agric. Food Chem., 51, 4990-4994.

Hemleben, V., 1981. Anthocyanin carrying structures in specific genotypes of *Matthiola incana* R. Br. Z. Naturforsch 36c, 926-927.

Kubo, H., Nozue, M., Kawasaki, K., Yauda, H., 1995. Intravacuolar spherical bodies in *Polygonium cuspidatum*. Plant Cell Physiol. 36, 1453-1458.

Markham, K. R., Gould, K. S., Winefield, C. S., Mitchell, K. A., Bloor, S. J., Boase, M. R., 2000. Anthocyanic vacuolar inclusions—their nature and significance in flower colouration. Phytochemistry 55 (2000) 327-336.

Nozzolillo, C., Ishikura, N., 1988. An investigation of the intracellular site of anthocyanins using isolated protoplasts and vacuoles. Plant Cell Rep. 7, 389.

Nozue, M., Kubo, H., Nishimura, M., Yasuda, H., 1995. Detection and characterization of a vacuolar protein (VP24) in anthocyanin-producing cells of sweet potato in suspension culture. Plant Cell Physiol. 36, 883-889.

Small C. J., Pecket, R. C., 1982. The ultrastructure in anthocyanoplasts in red-cabbage. Planta 154, 97-99.

Zhang et al., 2006, New insight into the structures and formation of anthocyanic vacuolar inclusions in flower petals. BMC Plant Biology 6, Art 29.

The invention claimed is:

1. A method of coloring a product under conditions in which free, or unbound anthocyanins are unstable, the method comprising adding-anthocyanic vacuolar inclusions that have been isolated from a lisianthus plant, to the product, wherein the product is a cosmetic product or a topical cream that has a pH in the range from about 4.0 to about 7.0 and wherein the product has a different color as a result of being colored with the anthocyanic vacuolar inclusions than the product would have had if it had not been colored with the anthocyanic vacuolar inclusions.

2. The method of claim 1, wherein the conditions are selected from:
  a) acidic pH and 37° C. for at least about 120 hours;
  b) a pH range greater than 4.0; and
  c) a light intensity of 10 µmol photons $m^{-2}$ $s^{-1}$ for at least about 72 hours.

3. The method of claim 1, that includes the step of isolating the anthocyanic vacuolar inclusions from the lisianthus plant before adding the isolated anthocyanic vacuolar inclusions to the product.

4. The method of claim 1, wherein the anthocyanic vacuolar inclusions are added to the product as part of an isolated anthocyanic vacuolar inclusion composition that is at least 50% pure anthocyanic vacuolar inclusions.

5. The method of claim 1, wherein the anthocyanic vacuolar inclusions are freeze-dried.

6. The method of claim 1, wherein the product has a pH in the range from 5 to 6.

7. The method of claim 1, wherein the product is a cosmetic product.

8. The method of claim 1, wherein the product is a topical cream.

* * * * *